US010524725B2

(12) United States Patent
Jeanne (10) Patent No.: US 10,524,725 B2
(45) Date of Patent: Jan. 7, 2020

(54) DEVICE, SYSTEM AND METHOD FOR DETECTING APNOEA OF A SUBJECT (71) Applicant: KONINKLIJKE PHILIPS N.V., Eindhoven (NL)

(72) Inventor: Vincent Jeanne, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 315 days.

(21) Appl. No.: 15/315,396

(22) PCT Filed: Jun. 4, 2015

(86) PCT No.: PCT/EP2015/062532
§ 371 (c)(1),
(2) Date: Dec. 1, 2016

(87) PCT Pub. No.: WO2015/185706
PCT Pub. Date: Dec. 10, 2015

(65) Prior Publication Data
US 2017/0119304 A1 May 4, 2017

(30) Foreign Application Priority Data
Jun. 6, 2014 (EP) .................................... 14171536

(51) Int. Cl.
*A61B 5/0205* (2006.01)
*A61B 5/00* (2006.01)
(Continued)

(52) U.S. Cl.
CPC .......... *A61B 5/4818* (2013.01); *A61B 5/0077* (2013.01); *A61B 5/0205* (2013.01);
(Continued)

(58) Field of Classification Search
CPC ... A61B 5/4818; A61B 5/0077; A61B 5/0205; A61B 5/02416; A61B 5/0816; A61B 5/113; A61B 5/1135; A61B 5/7246
(Continued)

(56) References Cited

U.S. PATENT DOCUMENTS 4,289,142 A * 9/1981 Kearns ............... A61B 5/02455
600/529
4,387,722 A * 6/1983 Kearns ............... A61B 5/02455
378/95
(Continued)

FOREIGN PATENT DOCUMENTS

EP 0072601 2/1983
JP 2005-218507 8/2005
(Continued)

OTHER PUBLICATIONS

Verkruysse, et al., "Remote plethysmographic imaging using ambient light", Optics Express, vol. 16, No. 26, Dec. 2008.
(Continued)

*Primary Examiner* — Navin Natnithithadha (57) ABSTRACT

A device, system and method unobtrusively and reliably detect apnoea of a subject (2). An input unit (11) receives image data of subject. The image data includes a sequence of images over time. A cardiac activity extraction unit (12) extracts from the image data a cardiac activity signal representing the subject's cardiac activity from a skin area of the subject using remote photoplethysmography. A motion signal extraction unit (14) extracts from said image data a motion signal representing motion of a subject's body part caused by breathing of the subject. An analysis unit (16) determines a similarity between said cardiac activity signal and said motion signal. A decision unit (18) detects apnoea of the subject based on the determined similarity.

17 Claims, 4 Drawing Sheets

(51) Int. Cl.
*A61B 5/024* (2006.01)
*A61B 5/08* (2006.01)
*A61B 5/113* (2006.01)

(52) U.S. Cl.
CPC ........ *A61B 5/02416* (2013.01); *A61B 5/0816* (2013.01); *A61B 5/1135* (2013.01); *A61B 5/7246* (2013.01)

(58) Field of Classification Search
USPC ....... 600/481, 483, 484, 509, 513, 529, 534, 600/595
See application file for complete search history.

(56) References Cited

U.S. PATENT DOCUMENTS

| | | | | |
|---|---|---|---|---|
| 4,422,458 | A * | 12/1983 | Kravath | A61B 5/0809 600/484 |
| 4,803,997 | A | 2/1989 | Bowman | |
| 6,498,652 | B1 * | 12/2002 | Varshneya | A61B 5/113 356/477 |
| 6,816,266 | B2 * | 11/2004 | Varshneya | A61B 5/113 356/477 |
| 7,162,294 | B2 * | 1/2007 | Rowlandson | A61B 5/0205 600/513 |
| 8,562,526 | B2 * | 10/2013 | Heneghan | A61B 5/0507 600/301 |
| 8,824,757 | B2 * | 9/2014 | Kolthammer | A61B 6/032 382/107 |
| 9,124,777 | B2 | 9/2015 | Van Leest | |
| 9,155,475 | B2 * | 10/2015 | Xu | A61B 5/0073 |
| 9,301,710 | B2 * | 4/2016 | Mestha | A61B 5/0064 |
| 9,339,210 | B2 * | 5/2016 | Kersten | A61B 5/0816 |
| 9,364,155 | B2 * | 6/2016 | Bardy | A61B 5/02055 |
| 9,545,228 | B2 * | 1/2017 | Bardy | A61B 5/02055 |
| 9,615,749 | B2 * | 4/2017 | Clifton | A61B 5/0205 |
| 9,659,229 | B2 * | 5/2017 | Clifton | A61B 5/0205 |
| 9,907,474 | B2 * | 3/2018 | Den Brinker | A61B 5/7203 |
| 9,928,607 | B2 * | 3/2018 | Jeanne | A61B 5/7207 |
| 9,943,371 | B2 * | 4/2018 | Bresch | A61B 5/0077 |
| 9,955,911 | B2 * | 5/2018 | Bardy | A61B 5/02055 |
| 9,996,917 | B2 * | 6/2018 | Jeanne | A61B 5/1171 |
| 2003/0095263 | A1 * | 5/2003 | Varshneya | A61B 5/113 356/477 |
| 2009/0203972 | A1 * | 8/2009 | Heneghan | A61B 5/0507 600/301 |
| 2010/0160798 | A1 * | 6/2010 | Banet | A61B 5/02125 600/490 |
| 2011/0311119 | A1 | 12/2011 | Vincent | |
| 2012/0157860 | A1 | 6/2012 | Suzuki | |
| 2013/0245502 | A1 | 9/2013 | Lange | |
| 2013/0342756 | A1 * | 12/2013 | Xu | A61B 5/0073 348/370 |
| 2014/0205165 | A1 * | 7/2014 | Jeanne | A61B 5/1171 382/128 |
| 2014/0275832 | A1 * | 9/2014 | Muehlsteff | A61B 5/0205 600/301 |
| 2014/0276098 | A1 * | 9/2014 | Bresch | A61B 5/7235 600/476 |
| 2014/0276104 | A1 * | 9/2014 | Tao | A61B 5/7239 600/476 |
| 2014/0303454 | A1 * | 10/2014 | Clifton | A61B 5/0205 600/301 |
| 2014/0334697 | A1 * | 11/2014 | Kersten | A61B 5/0816 382/128 |
| 2015/0105670 | A1 * | 4/2015 | Bresch | A61B 5/0077 600/479 |
| 2015/0332457 | A1 * | 11/2015 | Mestha | G06K 9/00362 382/103 |
| 2015/0379370 | A1 * | 12/2015 | Clifton | A61B 5/0205 382/128 |
| 2016/0174887 | A1 * | 6/2016 | Kirenko | A61B 5/14552 600/332 |
| 2016/0220128 | A1 * | 8/2016 | Den Brinker | A61B 5/7203 |
| 2016/0253820 | A1 * | 9/2016 | Jeanne | A61B 5/7207 382/107 |

FOREIGN PATENT DOCUMENTS

| | | | |
|---|---|---|---|
| WO | 2009/138976 | 11/2009 | |
| WO | 2010/100594 | 9/2010 | |
| WO | 2011143631 | 11/2011 | |
| WO | 2013027141 | 2/2013 | |
| WO | WO2013027027 A3 * | 2/2013 | ........... A61B 5/0205 |
| WO | 2013040511 | 3/2013 | |

OTHER PUBLICATIONS

Jae Hyuk Shin et al.: "Nonconstrained Sleep Monitoring System and Algorithms using Air-Mattress with Balancing Tube Method", IEEE Transactions on information technology in biomedicine, IEEE Service Center, Los Alamitos, CA, US, vol. 14, No. 1, Jan. 1, 2010 (Jan. 1, 2010), pp. 147-156.

Andrew Liszewski, "Philips' Vital Signs Camera App Measures Your Heart Rate, Lets Your iPad 2 Play Doctor", Nov. 17, 2011 https://gizmodo.com/philips-vital-signs-camera-app-measures-your-heart-rate-5860652.

* cited by examiner

DEVICE, SYSTEM AND METHOD FOR DETECTING APNOEA OF A SUBJECT

CROSS REFERENCE TO RELATED APPLICATIONS

This application is the U.S. National Phase application under 35 U.S.C. § 371 of International Application No. PCT/EP2015/062532, filed Jun. 4, 2015, published as WO 2015/185706 on Dec. 10, 2015, which claims the benefit of European Patent Application Number 14171536.7 filed Jun. 6, 2014. These applications are hereby incorporated by reference herein.

FIELD OF THE INVENTION

The present invention relates to a device and system for detecting apnoea of a subject, such as a person or animal. The present invention relates further to a method for detecting information allowing the detection of apnoea of a subject and to a computer program for implementing said method on a computer.

BACKGROUND OF THE INVENTION

Vital signs of a person, for example the heart rate (HR) or respiratory information (respiratory parameters) such as the respiratory rate (RR), can serve as a powerful predictor of serious medical events. For this reason the respiratory rate and/or the heart rate are often monitored online in intensive care units or in daily spot checks in the general ward of a hospital. Besides the heart rate, the respiratory rate is one of the most important vital signs. Both, the HR and the RR are still difficult to measure without having direct body contact. In present intensive care units, thorax impedance plethysmography or the respiratory inductive plethysmography are still the methods of choice for measuring the RR, wherein typically two breathing bands are used in order to distinguish thorax and abdominal breathing motion of a person. The HR is typically measured by use of electrodes, fixed at the chest of the subject, wherein the electrodes are connected to remote devices through cables. However, these obtrusive methods are uncomfortable and unpleasant for the patient being observed.

Moreover, unobtrusive respiratory rate measurements can be accomplished optically by use of a stationary video camera. A video camera captures the breathing movements of a patient's chest in a stream of images. The breathing movements lead to a temporal modulation of certain image features, wherein the frequency of the modulation corresponds to the respiratory rate of the patient monitored. Examples of such image features are the average amplitude in a spatial region of interest located around the patient's chest, or the location of the maximum of the spatial cross correlation of the region of interest in subsequent images.

Further, one or more video cameras are used for unobtrusively monitoring the HR, the RR or other vital signs of a subject by use of remote photoplethysmographic imaging. Remote photoplethysmographic imaging is, for instance, described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while the pixel average over a selected region (typically part of the cheek in this system) is calculated. By looking at periodic variations of this average signal, the heart rate and respiratory rate can be extracted. There are meanwhile a number of further publications and patent applications that describe details of devices and methods for obtaining vital signs of a patient by use of remote PPG.

Thus, the pulsation of arterial blood causes changes in light absorption. Those changes observed with a photodetector (or an array of photodetectors) form a PPG (photoplethysmography) signal (also called, among other, a pleth wave). Pulsation of the blood is caused by the beating heart, i.e. peaks in the PPG signal correspond to the individual beats of the heart. Therefore, a PPG signal is a heart rate signal in itself. The normalized amplitude of this signal is different for different wavelengths, and for some wavelengths it is also a function of blood oxygenation or other substances found in blood or tissue.

With respect to camera based systems, a superposition of vital sign signals, such as a respiratory rate signal superimposed by a heart rate signal or vice versa, adversely affect the determination of respiratory information. Such a superposition of vital signs can e.g. be measured, when a camera system observes the thorax motion of a subject, wherein the thorax motion due to breathing is superimposed by movements related to heart rate signals, so-called cardiac seismograms. These superimposed signals can have a comparable magnitude and even a comparable frequency. This might lead to dangerous situations, in particular during a period without breathing. Errors can occur that are related to the superimposed heart rate signal, which could give the impression that a respiratory rate is detected, in which an apnoea phase is present.

Episodes of apnoea often appear in premature babies as well as in adult population suffering from sleep related diseases. The common manner to monitor apnoea consists in placing contact sensors, in a rather obtrusive way, to the patient. These ranges from nasal thermocouples, respiratory effort belt transducer, piezoelectric transducer, optical sensor and electrocardiography ECG. Next to being really obtrusive these sensors are also prone to wrong measurement as some implementation cannot distinguish breathing from motion and most require calibration.

Jae Hyuk Shin et al.: "Nonconstrained Sleep Monitoring System and Algorithms using Air-Mattress with Balancing Tube Method", IEEE Transactions on information technology in biomedicine, IEEE Service Center, Los Alamitos, Calif., US, vol. 14, no. 1, 1 Jan. 2010 (2010-01-01), pages 147-156 discloses a bed-type sensor system using the air-mattress with balancing tube (AMBT) method to non-invasively monitor the signals of heartbeat, respiration, and events of snoring, sleep apnea and body movement of subject on the system. The proposed system consists of multiple cylindrical air cells, two sensor cells and 18 support cells. Small physiological signals are measured by the changes in pressure difference between the sensor cells, and the DC component was removed by balancing tube that is connecting the sensor cells. Using the AMBT method heartbeat, respiration, snoring, and body movement signals were clearly measured.

EP 0 072 601 A1 discloses a respiration monitor and x-ray trigger apparatus wherein analog respiration signals are amplified and divided into respiratory and heartbeat components. A trigger signal is selectively generated to the x-ray machine just prior to occurrence of a selected respiration extrema. Apnea alarms are generated if a predetermined decrease in respiration rate is detected in successive periods in conjunction with a predetermined number of decelerating heartbeats. An alarm is also generated if the respiration and heart rates are equal for a predetermined number of periods or if the respiration or heart rates stray outside of preset threshold values.

SUMMARY OF THE INVENTION

It is an object of the invention to provide a device and system for detecting apnoea of a subject and a method for detecting information allowing the detection of apnoea of a subject that unobtrusively allow a better accuracy and reliability of the detection while improving the comfort of subject.

In an aspect of the present invention a device for obtaining vital sign information of a subject is presented, said device comprising:

an input unit for receiving image data of subject, said image data including a sequence of images over time, a cardiac activity extraction unit for extracting from said image data a cardiac activity signal representing the subject's cardiac activity from a skin area of the subject using remote photoplethysmography, a motion signal extraction unit for extracting from said image data a motion signal representing motion of a subject's body part caused by breathing of the subject, an analysis unit for determining the similarity between said cardiac activity signal and said motion signal, and an decision unit for detecting apnoea of the subject based on the determined similarity.

In another aspect of the present invention, a system for detecting apnoea of a subject is presented, said system comprising:

an imaging unit for acquiring image data of subject, said image data including a sequence of images over time, and a device as claimed in claim 1 for detecting apnoea of a subject based on the acquired image data.

In another aspect of the present invention, a method for detecting information allowing the detection of apnoea of a subject is presented, said method comprising:

receiving image data of subject, said image data including a sequence of images over time, extracting from said image data a cardiac activity signal representing the subject's cardiac activity from a skin area of the subject using remote photoplethysmography, extracting from said image data a motion signal representing motion of a subject's body part caused by breathing of the subject, determining the similarity between said cardiac activity signal and said motion signal, said similarity allowing the detection of apnoea of the subject.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a computer, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The present invention is based on the idea to detect apnoea, in particular central apnoea, by use of image data obtained by an image sensor, such as a video camera, and an analysis of the similarity between motion-induced vital signs (in particular breathing rate and heart rate) captured from a measurement area, such as the torso (e.g. chest and/or belly area), that reflects motion of a subject's body part caused by breathing of the subject and another measurement area containing visible skin, such as e.g. the cheeks or the forehead, that reflects colour-changes induced vital signs caused by pulsation of blood and captured using the remote PPG technology.

An advantage of the proposed idea is that it enables a fully unobtrusive monitoring of apnoea. It provides full comfort to the patient by being completely non-intrusive. The advanced algorithms used allow for an accuracy enabling applications in hospital settings where low false detection is guaranteed by excluding movement artefact from the vital signs based on the analysis of the image content.

The skin area is typically a region of the body having a good blood circulation. From such a skin area a heart rate signal can be extracted, related to the heart rate of the subject observed, in particular using a method well-known in the art in the field of remote photo-plethysmography (PPG). These known methods can comprise the analysis of subtle color changes of the skin regions of the person, wherein these subtle color changes are related to the heart rate. Such methods are known in the art and are commonly used for e.g. extracting heart rate information of a person from PPG signals.

The subject's body part from which a motion signal is obtained allowing the extraction of a motion signal related to the respiratory rate information of the subject is typically the chest or belly area of the person, but may also be the nose or even other areas of the body of the subject, where respiratory motion can be detected.

The term "vital sign" as used in the context of the present invention refers to a physiological parameter of a subject (i.e. a living being) and derivative parameters. In particular, the term "vital sign" comprises blood volume pulse-signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

In a preferred embodiment the analysis unit is configured to determine a similarity measure representing said similarity and the decision unit is configured to detect apnoea by comparing said similarity measure against a predetermined threshold and/or earlier determined similarity measures. By this comparison a quick and simple way information whether or not there is a sleep apnoea or a risk of a sleep apoea can be obtained. For instance, from similarity measures obtained earlier for the same subject a reliable decision can be made, e.g. if the device is configured as self-learning device.

Various measures may be obtained for use a similarity measures. In one embodiment the analysis unit is configured to determine the similarity by determining the correlation between said cardiac activity signal and said motion signal over a time window. During an apnoea the correlation between the two signals will be significantly larger than during the absence of an apnoea so that the correlation is useable as reliable similiarity measure. For this purpose, for instance a Pearson's correlation coefficient of two variables X & Y=Corr(X,Y)=Covariance(X,Y)/(std(X)*std(Y)) may be used.

In another embodiment the analysis unit is configured to determine the similarity by comparing fundamental frequencies present in said cardiac activity signal and said motion signal. During an apnoea the motion signal will mainly show a fundamental frequency at the heart rate of the subject while in the absence of apnoea the motion signal will show a fundamental frequency at the heart rate and at the breathing rate.

In a further embodiment exploiting this the analysis unit is configured to determine the similarity by determining the Euclidian distance between the fundamental frequencies, the ratio between the fundamental frequencies and/or the energy ratio of the fundamental frequencies, in particular at the heart rate frequency.

Preferably, the proposed device further comprises a movement detection unit for detecting movement of at least a part of the subject by use of said image data, wherein the decision unit is configured to take detected movement into account in the detection of apnoea of the subject based on the determined similarity. The detected movement information may thereby characterize a body part or the complete body of the subject. Since such movements may negatively influence the detection of apnoea the movement information is preferably used to ignore or correct measurements of the cardiac activity signal and the motion signal. Since the movement information is obtained from the image data, e.g. by use of commonly known motion detection algorithms, no separate sensors are required according to this embodiment.

In an alternative embodiment the input unit is configured to receive movement information representing movement of at least a part of the subject, wherein the decision unit is configured to take the received movement information into account in the detection of apnoea of the subject based on the determined similarity. For detecting such movements various embodiments exist. For instance, body sensors (such as accelerators) or sensors external to the body (such as pressure sensors or capacitive sensors in a mattress) may be used for this purpose as conventionally known.

Preferably, in an embodiment the device comprises a measurement area detection unit for detecting in said image data a skin area for extraction of said cardiac activity signal and/or a body part area for extraction of said motion signal. Preferably, said detection is performed by means of image segmentation and/or object detection. Alternatively, a user may indicate in an image the respective areas, e.g. by use of a pointer or computer mouse.

Preferably, said system comprises an imaging unit, such as a single camera (e.g. a webcam or a video camera) for detecting electromagnetic radiation at least in the visible and/or infrared spectral range. When observing the subject, vital sign signals, especially the heart rate signal and the signal related to respiratory information, can be derived from slight variations in the radiation emitted, e.g. infrared light, and/or reflected e.g. visible light. For everyday applications it could be appreciated if mainly visible light is detected and analysed. For an application during a sleep period of the person, wherein the ambient light conditions are quite poor, it could also be advantageous to detect infrared light emitted or reflected from the person. To this end, besides common natural or artificial light sources no further radiation sources are required and/or have to be considered during analysis.

Preferably, the imaging unit (e.g. the camera) comprises a field of view covering both the skin area of the subject and the body portion of the subject. By way of example, the field of view of the camera can be adjusted such that the chest of the subject and the face of the subject are covered by the field of view of the camera. The image is typically acquired by an image sensor comprising a plurality of pixels arranged in a two-dimensional matrix. To clearly distinguish the skin portion from the body portion, spatially separated detection windows can be defined to clearly distinguish both portions from one another.

According to another embodiment of the present invention the device further comprises a user interface for entering information allowing for selecting and/or predefining the skin area and/or the body part. It is to be understood that the user can on the one hand manually predefine the field of view of the imaging unit or the analysis unit such, that the chest and the face of the person are enclosed within the field of view. This is a rough estimation, since the parameters related to the subject can vary over time, by way of example, when the person moves or the person is at least partially covered with cloth or a blanket. On the other hand the field of view of the imaging unit can be adapted automatically to have an optimized aspect ratio between the portions that shall be observed and the background. For this purpose, the subject may carry one or more markers or orientation indicators detectable by the camera allowing for adapting the field of view in an optimized manner. By way of example, in a hospital the marker or the orientation indicator is typically attached to the body, especially at the skin portion or at the body portion of a patient, which are to be observed. Therefore, the device can be adapted to find these markers, and adapt the field of view in a way that both, the skin area and the body part, are well-positioned within the field of view.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
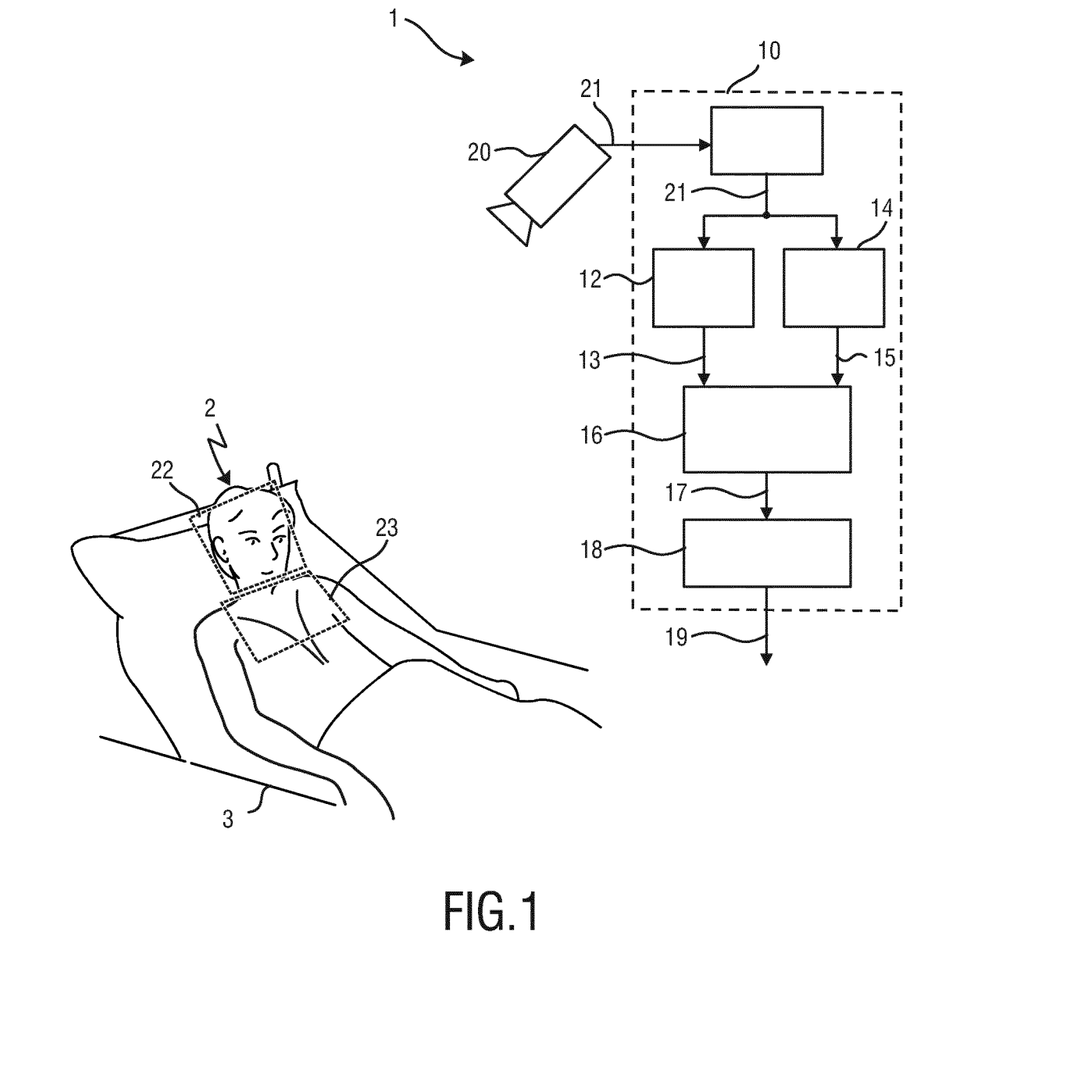
FIG. 1 shows a first exemplary embodiment of a device and system for detecting apnoea of a subject according to the present invention.

FIG. 1 shows a first exemplary embodiment of a device 10 and a system 1 for detecting apnoea of a subject 2 (here a person, e.g. a patient in a hospital or an elderly person in a care environment) according to the present invention. In this embodiment the subject 2 lies in a bed 3. Besides the device 10 the system 1 comprises an imaging unit 20, e.g. a camera, for acquiring image data 21 of the subject 2, said image data including a sequence of images over time, based on which the device 10 detects apnoea of the subject 2.

The device 10 comprises an input unit 11 for receiving the image data of the subject 2, either directly and on the fly from the imaging unit 20. A cardiac activity extraction unit 12 is provided for extracting from said image data 21 a cardiac activity signal 13 representing the subject's cardiac activity from a skin area 22 of the subject 2 using remote photoplethysmography. A motion signal extraction unit 14 for extracting from said image data 21 a motion signal 15 representing motion of a subject's body part 24, e.g. the chest 23 within a body area 23 or the belly, caused by breathing of the subject 2. An analysis unit 16 for determining the similarity 17 between said cardiac activity signal 13 and said motion signal 15. Finally, a decision unit 18 detects apnoea of the subject 2 based on the determined similarity 17 and e.g. issues a corresponding signal 19, e.g. a warning to a nurse or a control monitor, if there is a certain (e.g. predetermined) likelihood of an apnoea.

Some or all elements of the device 10 can be implemented by separate elements (e.g. processors or software functions), but can also be represented and implemented by a common element, e.g. a common processing apparatus or a common software carried out by a processor or computer.

Figure 2:
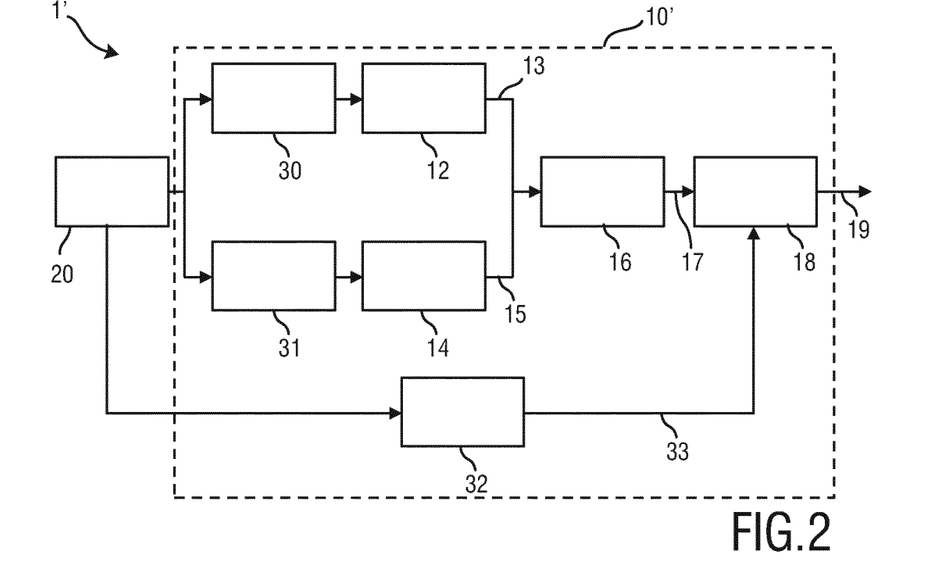
FIG. 2 shows a schematic diagram of a second exemplary embodiment of a device and system for detecting apnoea of a subject according to the present invention.

FIG. 2 shows a schematic diagram of a second exemplary embodiment of a device 10 and system 1' for detecting apnoea of a subject 2 according to the present invention. Identical elements as depicted in FIG. 1 are given the same reference numbers. The imaging unit 20 may also be referred to as acquisition module to capture visual information about a patient, such as the above mentioned image data 21. A measurement area detection unit 30, 31 per subsequent processing path receives the image data 21 (i.e. acts as input unit) and determines at least one measurement area per processing path (i.e. per vital sign of interest). In particular, a skin area 22 is detected by the measurement area detection unit 30 for extracting a cardiac activity signal 13 from it and a body area 23 is detected by the measurement area detection unit 31 for extracting a motion signal 15. The respective signals 13, 15 are then extracted from the respective areas detected within the image data by use of the cardiac activity extraction unit 12 and the motion signal extraction unit 14. The analysis unit 16 compares the similarity of the extracted cardiac activity signal 13 and the extracted motion signal 15, e.g. to generate a similarity value or any other similarity measure 17 so that finally the decision unit 18 can characterize the status of an apnoea event and issue a corresponding information signal 19.

An optional movement detection unit 32 is provided that detects movement of at least a part of the subject 2 by use of said image data. The detected movement information 33 is then provided to the decision unit 18 to improve the characterization of an apnoea event, e.g. to assess the quality of a measurement.

It shall be noted that the skin area 22 and the body area 23 are generally detected within the same image data. In other embodiments, however, there are separate streams of image data, e.g. acquired by different cameras. Further, instead of automatic detection of these areas 22 and 23, a manual detection, e.g. by a user through an input device such as a pointer or computer mouse, may be applied as well.

In the following details of the steps applied in the units of the proposed device will be explained.

The imaging unit 20 comprises at least one image sensor sensitive to at least one wavelength characterized in the visible or near-infrared part of the light spectrum. Depending on the embodiment, the imaging unit 20 also includes an illumination source at the wavelength of interest. The image acquisition is preferably performed at a minimum rate of 7 Hz (minimum sampling rate required according to Nyquiyst for heart rate extraction).

The measurement area detection unit 30 detects a measurement area from which the cardiac activity (i.e. heart rate related information) can be extracted by use of remote PPG technology. The measurement area used for this is focused mainly at the skin of the subject, preferably located on the facial area which provides the strongest PPG signal for heart rate extraction.

To detect this measurement area various options exist. For instance, in an embodiment automatic skin detection is applied where several wavelengths are used. This embodiment can range from using the native RGB wavelengths (color channels) of the video stream and performing a segmentation to detect skin in the known HSV color domain by selecting a given portion of the Hue. Instead, multiple RGB and IR wavelengths may be used as e.g. proposed in Kanzawa Y. et al., Human Skin Detection by Visible and Near-Infrared Imaging, MVA2011 IAPR Conference on Machine Vision Applications, Jun. 13-15, 2011, Nara, JAPAN. Further, any body part detector (e.g. for detecting the face) can be used to extract a skin color and segment the image based on the detected skin color.

In another embodiment object detection techniques as proposed by Viola-Jones (see e.g. P. Viola, M. Jones: Robust Real-time Object Detection, 2001) are used, which can be operated regardless of the number of wavelengths used by the imaging unit.

In still another embodiment detecting a kind of living pixels (i.e. pixels in a region of interest that exhibits color variations induced by change in blood flow) as described in US 2011/311119 A1, which is herein incorporated by reference, can be used. In this application a method of processing images of at least one living being is described including obtaining a sequence of digital images taken at consecutive points in time. At least one measurement zone comprising a plurality of image points is selected. For each measurement zone, a signal representative of at least variations in a time-varying value of a combination of pixel values at least a number of the image points for use in determining at least one of a presence and a frequency value of at least one peak in a spectrum of the signal corresponding to a frequency of a periodic physiological phenomenon is obtained. The step of selecting at least one measurement zone includes analyzing information based on pixel data of a plurality of image parts in at least one of the images, each image part including at least one image point, and selecting each measurement zone from contiguous parts determined to have similar characteristics.

The measurement area detection unit 31 detects a measurement area used for the extraction of breathing-rate related information. The detection is preferably focused mainly at the chest/belly of the subject. To detect this area various options exist. For instance, in an embodiment object detection techniques as proposed by Viola-Jones (e.g. as cited above), which can be operated regardless of the number of wavelengths used by the imaging unit.

In another embodiment so-called breathing pixels (i.e. pixels in a region of interest that exhibits motion patterns induced by breathing as described in European patent application 13157242 and subsequent applications claiming priority from said European patent application can be detected. This document discloses an apparatus and method for determining vital sign information from a subject, comprising a detection unit for detecting radiation from a field of view and for determining characteristic parameter including vital sign information of the subject from different areas of the field of view, a frequency analysis unit for determining a spectral parameter of the characteristic parameter derived from the different areas, a selection unit for selecting at least one of the areas of the field of view on the basis of the spectral parameter, and a calculation unit for calculating the vital sign information on the basis of the characteristic parameter from the at least one selected area.

It is to be understood, that in further embodiments, the skin area can also be the arm or other detectable skin areas of the subject and the body portion can also include the mouth and/or the nose of the subject.

The cardiac activity extraction unit 12 preferably performs the extraction of the cardiac activity signal 13 by use of remote PPG, as explained above, from the detected skin area(s). A typical cardiac activity signal 13 is shown in FIG. 3A.

The motion signal extraction unit 14 preferably performs the extraction of the motion signal 15 by use of image processing methods, e.g. by detecting physical motion of the chest or belly area. A typical motion signal 15 is shown in FIG. 3B.

Figure 3A:
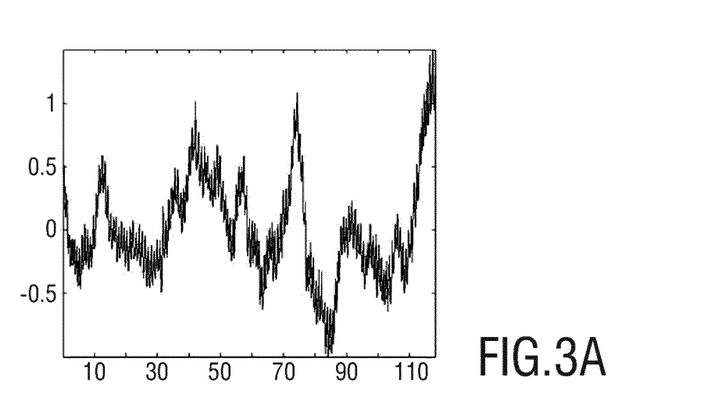
FIG. 3 shows diagrams of a cardiac signal and of a motion signal as used according to the present invention.
Figure 3B:
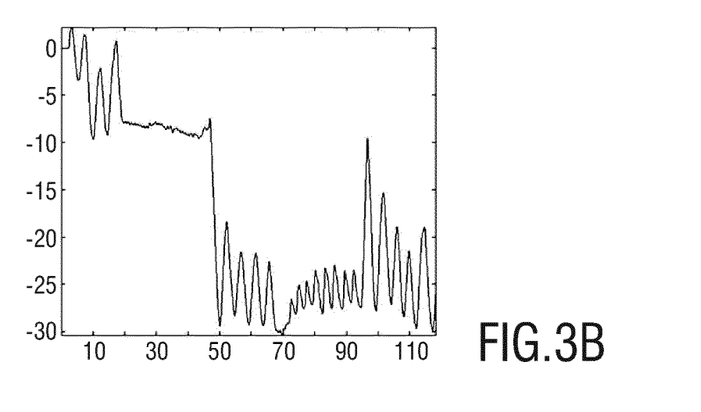

From the two signals shown in FIGS. 3A and 3B it can be seen that between second 22 and second 47 an apnoea moment occurs. This is characterized by a flat line in the motion signal 15 shown in FIG. 3B.

The main purpose of the analysis unit 16 is to analyse the similarity between motion-induced vital signs (i.e. the motion signal 15) captured preferably from the torso and colour-changes induced vital signs (i.e. the cardiac activity signal 13) captured using the remote PPG technology. When a living being stop breathing, e.g. shows a central apnoea, no real "breathing signal" is captured by the camera-based motion signal extraction unit 14 focused at the motion of the torso. Instead, the signal captured by this unit reflects the mechanical activity of the heart; this phenomenon is for example used in the measurement technique called cardio-ballistography.

Based on this observation, the decision unit 18 is (preferably continuously or at regular intervals) performing a similarity analysis between the two vital signs 13, 15 extracted from the image data.

Preferably, this analysis comprises extracting the correlation between these two signals 13, 15 over a given time window. During central apnoea both signals will exhibit a strong correlation as they both are a representation of the cardiac activity, while under normal circumstances this correlation will be significantly reduced since they originate from "uncorrelated" phenomenon.

Figure 4A:
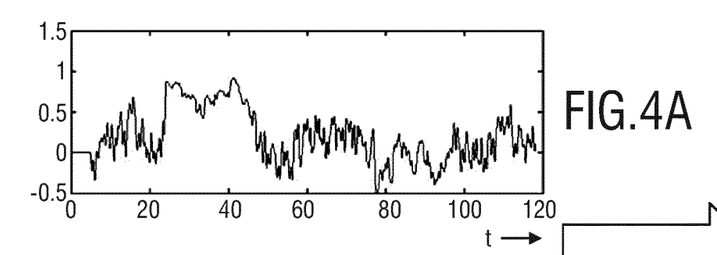
FIG. 4 shows diagrams of correlation signals used in an embodiment of the present invention.
Figure 4B:
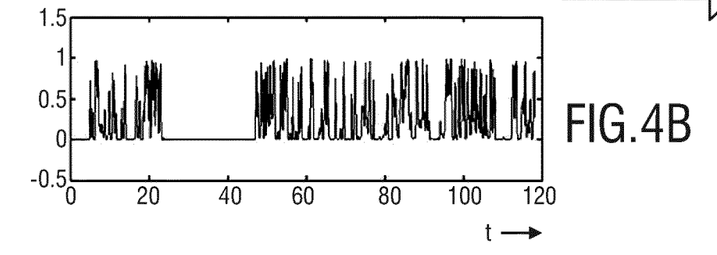
Figure 4C:
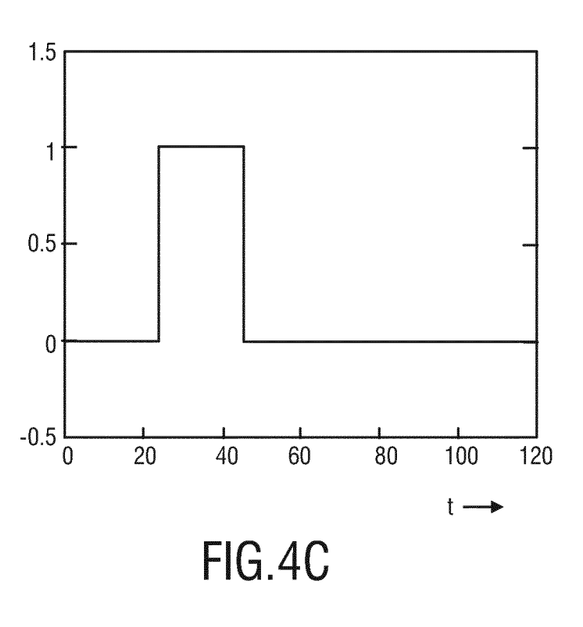

FIG. 4 illustrates the embodiment where the correlation between the two signals 13, 15 is used. FIG. 4A shows the r-value of the correlation between the two signals and FIG. 4B shows the p-value of the correlation between the two signals. FIG. 4C shows a generated result signal indicating when an apnoea has been detected. In these figures it can be seen that when the apnoea moment occurs, the correlation between these two signals increases significantly (i.e. the well-known r-value >0.7 and the well known p-value <$10^{-9}$). This is due to the fact that at that moment the motion signal contains heart rate information induced by motion of the chest.

The significance of the correlation may be defined as follows, wherein R is the actual coefficient of the correlation:

$$R(i, j) = \frac{C(i, j)}{\sqrt{C(i, i)C(j, j)}}.$$

The p-value is computed by transforming the correlation to create a t statistic having n−2 degrees of freedom, where n is the number of rows of X. The confidence bounds are based on an asymptotic normal distribution of 0.5*log((1+R)/(1−R)), with an approximate variance equal to 1/(n−3). These bounds are accurate for large samples when X has a multivariate normal distribution. The 'pairwise' option can produce an R matrix that is not positive definite.

In still another embodiment, the analysis is based on the characterization of the fundamental frequencies of both signals. Under normal circumstances (no apnoea), the two signals originating from colour analysis and motion analysis will respectively exhibit a fundamental frequency at the heart rate and at the breathing-rate. However, when no breathing occurs, the motion signal originating from the torso area will exhibit a fundamental frequency representative of the heart activity as it originates not from breathing induced motion but from cardiac induced motion.

Figure 5A:
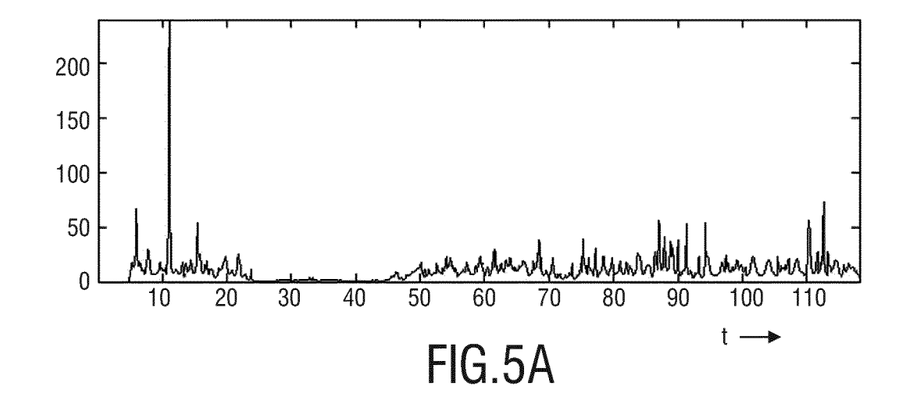
FIG. 5 shows a diagram of an energy signal used in an embodiment of the present invention.
Figure 5B:
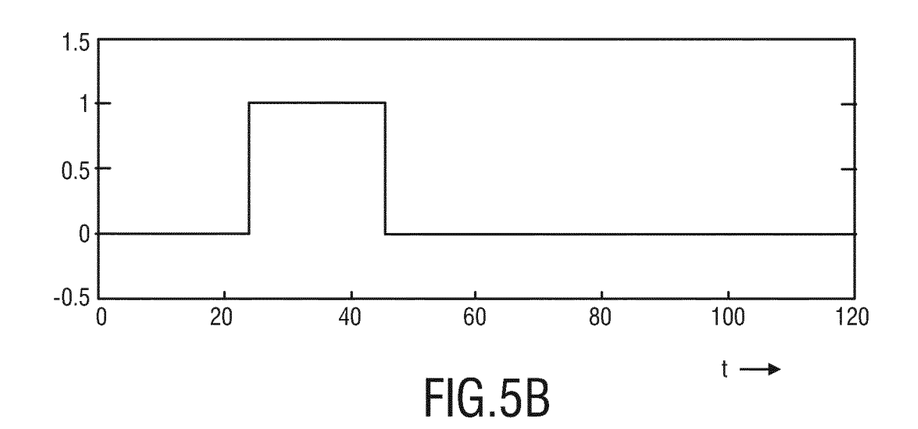

This is illustrated in FIG. 5, in which FIG. 5A represents the ratio of energy contained in both signals at the heart rate frequency and FIG. 5B shows the result signal. It can be seen that when the apnoea moment occurs, both signals' energy is similar and concentrated at the heart rate frequency.

In this embodiment, the similarity can preferably be expressed by computing the Euclidian distance between both fundamental frequencies, their frequency ratio and/or their energy ratio at the heart rate frequency.

Optionally, as shown also in FIG. 2, movement analysis is performed in a movement analysis unit 32 on at least one relevant part of the image data acquired by the imaging unit 20. This relevant area can characterize the entire subject or subparts of it. The detection of this area can be based on the detection of specific pixel properties (e.g. color for skin detection) or on object detection methods as proposed by ViolaJones as cited above. Once defined, spatio-temporal processing like 3DRS or Optical Flow may be used to determine motion characteristics, such as intensity, direction, uniformity, etc. The detected movement information 33 is provided to the decision unit 18.

In another embodiment the movement information is not detected by the device 10, 10' itself, but the device 10, 10' receives movement information representing movement of at least a part of the subject. Said movement information may e.g. be detected by separate sensors (4 in FIG. 1), e.g. accelerometers attached to the subject's body or pressure sensors provided in a mattress.

Based on the similarity information 17, e.g. a similarity measure, outputted by the analysis 16, the detection unit 18 characterizes the data analysed as an apnoea event or not. In one embodiment, the similarity measure is compared against an empirically determined value. In another embodiment, the similarity measure is compare against an empirically determined value and a posterior similarity value to take temporal dynamics into account. In still another embodiment, the similarity value is weighted by using at least one movement property derived by the movement analysis unit 32. Doing so, a false event one can be fully ignored when too much movement occurs and disturbs the measurement.

The proposed system, device and method are particularly relevant for patient monitoring applications ranging from hospital environment to home settings (e.g. elderly monitor, smart baby monitor, ICU or NICU monitoring, etc.).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical monitor device for detecting apnoea of a subject, comprising:
    a video camera configured to monitor the subject and generate image data indicative thereof, said image data including a sequence of images over time,
    an input unit for receiving the image data of subject from the video camera,
    a cardiac activity extraction unit for extracting from said image data a cardiac activity signal representing the subject's cardiac activity from a skin area of the subject using remote photoplethysmography,
    a motion signal extraction unit for extracting from said image data a motion signal representing motion of a subject's body part caused by breathing of the subject,
    an analysis unit for determining the similarity between said cardiac activity signal and said motion signal, and
    a decision unit for detecting apnoea of the subject based on the determined similarity, and generating an apnoea warning signal in response to detecting the apnoea,
    wherein the motion signal represents motion of the subject's body part caused by the breathing of the subject and motion of the subject's body part caused by cardiac activity of the subject such that the motion signal has a fundamental frequency of a respiratory rate of the subject when the subject is breathing and has a fundamental frequency of a heart rate of the subject during apnoea, and wherein
        during apnoea, the cardiac activity signal and the motion signal have a higher similarity, and
        when the subject is breathing normally, the similarity between the cardiac activity signal and the motion signal is lower.

2. The medical monitor device as claimed in claim 1, wherein the analysis unit is configured to determine a similarity measure representing said similarity, and wherein the decision unit is configured to detect apnoea by comparing said similarity measure against a predetermined threshold and/or earlier determined similarity measures.

3. The medical monitor device as claimed in claim 1, further comprising:
    a movement detection unit for detecting movement of at least a part of the subject by use of said image data,
    wherein the decision unit is configured to take detected movement into account in the detection of apnoea of the subject based on the determined similarity.

4. The medical monitor device as claimed in claim 1,
    wherein the input unit is configured to receive movement information representing movement of at least a part of the subject,
    wherein the decision unit is configured to take the received movement information into account in the detection of apnoea of the subject based on the determined similarity.

5. The medical monitor device as claimed in claim 1, further comprising:
    a measurement area detection unit for detecting in said image data a skin area for extraction of said cardiac activity signal and a body part area for extraction of said motion signal.

6. The medical monitor device as claimed in claim 5,
    wherein said measurement area detection unit is configured to detect the skin area and a body part area by segmenting the images.

7. The medical monitor device as claimed in claim 1,
    wherein the analysis unit is configured to determine the similarity by determining the correlation between said cardiac activity signal and said motion signal over a time window.

8. The medical monitor device as claimed in claim 1,
    wherein the analysis unit is configured to determine the similarity by comparing fundamental frequencies present in said cardiac activity signal and said motion signal.

9. The medical monitor device as claimed in claim 1, comprising:
    a motion sensor for acquiring motion information representing motion of at least a part of the subject.

10. The medical monitor device as claimed in claim 1,
    wherein the motion signal represents motion of the subject's body part caused by the breathing of the subject and motion of the subject's body part caused by cardiac activity of the subject, such that when the subject stops breathing, the motion signal represents cardiac activity.

11. A medical monitor for detecting apnoea of a subject, comprising:
    a video camera for generating image data of the subject, said image data including a sequence of images over time,
    an input unit for receiving the image data,
    a cardiac activity extraction unit for extracting from the received image data a cardiac activity signal representing cardiac activity of the subject from a skin area of the subject using remote photoplethysmography,
    a motion signal extraction unit for extracting from said received image data a motion signal representing motion of a subject's body part caused by breathing of the subject,
    an analysis unit configured to determine a similarity between said cardiac activity signal and said motion signal by:

comparing fundamental frequencies present in said cardiac activity signal and said motion signal, and determining a Euclidian distance between the fundamental frequencies, a ratio between the fundamental frequencies and/or an energy ratio of the fundamental frequencies, in particular at the heart rate frequency, and a decision unit for detecting apnoea of the subject based on the determined similarity and outputting an apnoea warning in response to detecting the apnoea.

12. A method of monitoring for apnoea in a subject, comprising:

receiving video image data of subject, said image data including a sequence of images over time, the images of the sequence each including (i) a skin area which changes color with cardiac activity and (ii) a body region which moves with respiration and cardiac motion, extracting from said video image data a cardiac activity signal representing the subject's cardiac activity from the skin area of the subject using remote photoplethysmography, extracting from said video image data a motion signal representing motion of the body region caused by breathing and cardiac activity of the subject, wherein during apnoea, the cardiac activity dominates the motion signal, determining a similarity measure between said cardiac activity signal and said motion signal indicating occurrence of apnoea of the subject when the similarity measure exceeds a predetermined threshold, in response to the motion signal indicating the occurrence of apnoea, generating an apnoea warning, wherein the motion signal represents motion of the subject's body part caused by the breathing of the subject and motion of the subject's body part caused by cardiac activity of the subject, such that when the subject stops breathing, the motion signal represents cardiac activity.

13. A non-transitory computer-readable medium carrying a computer program comprising program code configured to control a computer to carry out the steps of the method as claimed in claim 12 when said computer program is carried out on a computer.

14. A monitor for monitoring a subject for apnoea, comprising:

a camera configured to generate a sequence of images of at least a skin area and a body part area of the subject over time;

one or more computer processors configured to:

from a first portion of the images of the sequence corresponding to the skin area of the subject, extracting a cardiac activity signal using remote photoplethysmography, the cardiac activity signal representing cardiac activity of the subject;

from a second portion of the images of the sequence of images corresponding to the body part area of the subject, extracting a motion signal representing motion of the body part area of the subject, the motion signal representing breathing and cardiac activity motion of the body part area of the subject;

determining a similarity measure between the cardiac activity signal and the motion signal over time;

comparing the similarity measure with a threshold; and in response to the similarity measure meeting or exceeding the threshold, controlling an apnoea indicating device to indicate apnoea of the subject, wherein when the subject is breathing normally, the breathing motion dominates the motion signal and when the subject undergoes apnoea, the motion signal is dominated by the cardiac activity motion, and wherein when the cardiac activity motion dominates the motion signal, the similarity measure between the motion signal and the cardiac activity is high, and wherein when the subject is breathing normally, the motion signal is dominated by the breathing of the subject and the similarity measure is low.

15. The monitor as claimed in claim 14, wherein when the motion signal is dominated by cardiac activity motion, the motion signal has a fundamental frequency at a heart rate of the subject, wherein when the subject is breathing normally, the motion signal has a fundamental frequency at the breathing rate and wherein the cardiac activity signal has a fundamental frequency at the heart rate of the subject, and wherein the one or more computer processors are further configured to:

comparing the fundamental frequencies of the motion signal and the cardiac activity signal.

16. The monitor according to claim 15, wherein the one or more computer processors are further configured to:

determine at least one of a Euclidean distance between the fundamental frequencies, a ratio between the fundamental frequencies, and an energy ratio of the fundamental frequencies.

17. The monitor according to claim 15, wherein the one or more computer processors are further configured to:

determine the similarity between the fundamental frequencies of the motion signal and the cardiac activity signal at a frequency of a heart rate of the subject.

* * * * *